US009868242B2

(12) United States Patent
Dando et al.

(10) Patent No.: US 9,868,242 B2
(45) Date of Patent: *Jan. 16, 2018

(54) METHODS OF MANUFACTURING A MULTI-LUMEN DEVICE

(71) Applicant: Medtronic Ablation Frontiers LLC, Minneapolis, MN (US)

(72) Inventors: Jeremy D. Dando, Plymouth, MN (US); John B. Horrigan, Beverly, MA (US); Jeffrey J. Jannicke, Andover, MN (US); Michael E. Kapust, Tewksbury, MA (US); Neil Purcell, Galway (IE)

(73) Assignee: Medtronic Ablation Frontiers LLC, Minneapolis, MN (US)

( * ) Notice: Subject to any disclaimer, the term of this patent is extended or adjusted under 35 U.S.C. 154(b) by 721 days.

This patent is subject to a terminal disclaimer.

(21) Appl. No.: 14/262,025

(22) Filed: Apr. 25, 2014

(65) Prior Publication Data
US 2015/0306805 A1    Oct. 29, 2015

(51) Int. Cl.
*B29C 47/00*    (2006.01)
*B29C 47/06*    (2006.01)
(Continued)

(52) U.S. Cl.
CPC ........ *B29C 47/0028* (2013.01); *B29C 47/003* (2013.01); *B29C 47/0026* (2013.01);
(Continued)

(58) Field of Classification Search
None
See application file for complete search history.

(56) References Cited

U.S. PATENT DOCUMENTS 2,936,761 A    5/1960 Snyder
3,901,965 A    8/1975 Honeyman, III
(Continued)

FOREIGN PATENT DOCUMENTS

JP    6054830 A    3/1985
WO   9965557 A2   12/1999
(Continued)

OTHER PUBLICATIONS

International Search Report and Written Opinion dated Jul. 17, 2015, for corresponding International Application No. PCT/US2015/026835; International Filing Date: Apr. 21, 2015 consisting of 10 pages.

(Continued)

*Primary Examiner* — Monica Huson
(74) *Attorney, Agent, or Firm* — Christopher & Weisberg, P.A.

(57) ABSTRACT

A method and system for manufacturing a multi-lumen device that includes extruding a first layer of material to form an elongate body with a first lumen and a second lumen, the elongate body having a length of at least 100 feet, depositing a mesh layer over the first layer of material along the entire length of the elongate body, and extruding a second layer of material over the mesh layer along at least a portion of the length of the elongate body. The length of at least 100 feet may be considered a first length, the method further comprising cutting the elongate body into a plurality of shortened elongate bodies having a usable length, such as between approximately two feet and approximately six feet.

22 Claims, 11 Drawing Sheets

(51) Int. Cl.
| | |
|---|---|
| *B29C 47/08* | (2006.01) |
| *B29C 47/02* | (2006.01) |
| *B29C 47/04* | (2006.01) |
| *B29C 47/90* | (2006.01) |
| *B29C 47/92* | (2006.01) |
| *B29C 49/78* | (2006.01) |
| *B29C 47/88* | (2006.01) |
| *A61M 25/00* | (2006.01) |
| *B29K 101/12* | (2006.01) |
| *B29L 31/00* | (2006.01) |

(52) U.S. Cl.
CPC ........ B29C 47/0066 (2013.01); B29C 47/025 (2013.01); B29C 47/027 (2013.01); B29C 47/04 (2013.01); B29C 47/065 (2013.01); B29C 47/0869 (2013.01); B29C 47/8895 (2013.01); B29C 47/902 (2013.01); B29C 47/92 (2013.01); B29C 49/783 (2013.01); *A61M 25/0012* (2013.01); *A61M 25/0032* (2013.01); *A61M 2025/0036* (2013.01); *A61M 2207/10* (2013.01); *B29C 2793/009* (2013.01); *B29C 2947/92514* (2013.01); *B29C 2947/92904* (2013.01); *B29C 2947/92923* (2013.01); *B29K 2101/12* (2013.01); *B29K 2995/0056* (2013.01); *B29L 2031/7542* (2013.01)

(56) References Cited

U.S. PATENT DOCUMENTS

| | | | |
|---|---|---|---|
| 4,138,457 | A | 2/1979 | Rudd et al. |
| 4,699,157 | A | 10/1987 | Shonk |
| 4,898,702 | A | 2/1990 | Elkins et al. |
| 5,002,559 | A | 3/1991 | Tower |
| 5,063,018 | A | 11/1991 | Fontirroche et al. |
| 5,227,325 | A | 7/1993 | Gonzalez |
| 5,247,136 | A | 9/1993 | Mitsuyasu et al. |
| 5,669,920 | A | 9/1997 | Conley et al. |
| 5,676,659 | A | 10/1997 | McGurk |
| 5,690,613 | A | 11/1997 | Verbeek |
| 5,879,499 | A | 3/1999 | Corvi |
| 5,906,036 | A | 5/1999 | Pagan |
| 6,004,310 | A | 12/1999 | Bardsley et al. |
| 6,030,371 | A | 2/2000 | Pursley |
| 6,042,578 | A | 3/2000 | Dinh et al. |
| 6,159,198 | A | 12/2000 | Gardeski et al. |
| 6,186,986 | B1 | 2/2001 | Berg et al. |
| 6,251,092 | B1 | 6/2001 | Qin et al. |
| 6,582,536 | B2 | 6/2003 | Shimada |
| 6,733,486 | B1 | 5/2004 | El-Nounou et al. |
| 6,979,312 | B2 | 12/2005 | Shimada |
| 7,731,682 | B2 | 6/2010 | Bencini et al. |
| 7,732,682 | B1 | 6/2010 | Delzer |
| 9,505,159 | B2 * | 11/2016 | Dando ................ B29C 47/0026 |
| 2003/0135198 | A1 | 7/2003 | Berhow et al. |
| 2003/0145915 | A1 | 8/2003 | Shimada |
| 2011/0245806 | A1 | 10/2011 | Patterson |
| 2013/0123752 | A1 | 5/2013 | Pursley |
| 2014/0012193 | A1 | 1/2014 | Qiu et al. |
| 2015/0306805 | A1 | 10/2015 | Dando et al. |

FOREIGN PATENT DOCUMENTS

| | | |
|---|---|---|
| WO | 0160443 A1 | 8/2001 |
| WO | 2009075989 A1 | 6/2009 |
| WO | 2013146673 A1 | 10/2013 |

OTHER PUBLICATIONS

International Search Report and Written Opinion dated Jul. 8, 2015, for corresponding International Application No. PCT/US2015/026836; International Filing Date: Apr. 21, 2015 consisting of 10 pages.

International Search Report and Written Opinion dated Jul. 21, 2015, for corresponding International Application No. PCT/US2015/02683; International Filing Date: Apr. 21, 2015 consisting of 11 pages.

\* cited by examiner

METHODS OF MANUFACTURING A MULTI-LUMEN DEVICE

CROSS-REFERENCE TO RELATED APPLICATION n/a

STATEMENT REGARDING FEDERALLY SPONSORED RESEARCH OR DEVELOPMENT n/a

FIELD OF THE INVENTION

The present invention relates to methods and systems for manufacturing a steerable catheter and/or sheath for medical devices, in particular, intravascular and intracardiac sheaths.

BACKGROUND OF THE INVENTION

Medical devices such as intravascular and intracardiac catheters are commonly used for a variety of medical procedures, such as in cardiovascular, neurologic, endoscopic, neurovascular, renal, and other applications. For example, these steerable devices may be used in minimally invasive procedures such as cardiac ablation, mapping, stent delivery, and imaging. In performing procedures such as these, it is often desirable, if not essential, that the catheter is steerable in order to navigate the catheter through the patient's vasculature to the desired treatment location. For medical devices that are themselves not steerable, a steerable catheter sheath may be used to guide the medical device to a treatment desired treatment location.

Steerable sheaths and steerable catheters may include multiple longitudinal lumens. In the case of a steerable catheter, for example, the catheter body may include a major or central lumen through which a push rod, rigid or semi-rigid guidewire lumen, or shaft may be passed. In the case of a steerable sheath, for example, the sheath may include a major or central lumen through which a second device or catheter may be passed. In both cases, the catheter or sheath may include one or more minor lumens for one or more pull wires used for steering.

Manufacturing methods for steerable catheters and sheaths have improved over the years. Many such devices that once required tedious hand assembly or time-intensive ram extrusion can now be produced using extrusion techniques that allow for multilayer extrusion of a device. For example, a sheath may be produced with an inner layer consisting of a lubricious material such as polytetrafluoroethylene (PTFE), a middle layer consisting of a braided steel matrix for strength and torque transmission, and an outer layer consisting of a thermoplastic or similar material. Although the manufacturing process is becoming more efficient, there are still several aspects of steerable catheter and sheath production that are inefficient and costly.

One example of a limitation in steerable catheter and sheath production is the creation of the minor lumens. A thin layer of PTFE, for example, having a wall thickness of about 0.025 mm (approximately 0.001 inch), is commonly used for the minor lumens. Although this material is valued for its low coefficient of friction, it is not very rigid and easily collapses during the manufacturing process, particularly when used for the small-diameter minor lumens. To prevent collapse, a rigid mandrel is inserted into each minor lumen to prevent collapse during braiding, reflow, or other manufacturing steps. Although effective in maintaining patency of the minor lumens, the use of mandrels adds cost and complexity to the manufacturing process.

Additionally, extrusion may be used to manufacture steerable catheters and sheaths. However, these multi-lumen devices are commonly produced using a discrete extrusion and/or fusing method, in which a usable length of catheter body or sheath, for example, less than six feet (such as around three feet), is extruded at a time. Each length of catheter body or sheath may be manufactured in a series of steps or "passes." As an example, a polymer tube is extruded and cut to a desired length, creating discrete polymer tubes. Each tube is then slid over a length of mandrel, and a stainless steel braided wire mesh is overlayed over each discrete tube. Then, another polymer tube is slid over the mandrel, first polymer tube, and mesh layer, and the whole assembly is heated in an oven to fuse the materials together and create discrete lengths of catheter or sheath body. Undergoing each step for a discrete length of catheter or sheath is inefficient and adds increased labor requirements and operational costs.

It is therefore desired to provide efficient and cost-effective methods of manufacturing steerable catheter bodies and steerable sheaths. In one aspect, it is desirable to provide a method of manufacturing these multi-lumen devices without the need for a mandrel, which incurs additional production cost. In another aspect, it is desirable to provide a method of manufacturing these multi-lumen devices using an efficient extrusion process.

SUMMARY OF THE INVENTION

The present invention advantageously provides a method and system for producing a multi-lumen elongate body. In one embodiment, a method may include extruding a first layer of material to form an elongate body with a first lumen and a second lumen, the elongate body having a length of at least 100 feet, depositing a mesh layer over the first layer of material along the entire length of the elongate body, and extruding a second layer of material over the mesh layer along at least a portion of the length of the elongate body. The length of at least 100 feet may be considered a first length, the method further comprising cutting the elongate body into a plurality of shortened elongate bodies, each shortened elongate body having a second length that is less than the first length. For example, the second length may be less than approximately six feet. Each of the first lumen and the second lumen may be filled with a fluid during extruding the first layer, depositing the mesh layer, and extruding the second layer. Further, the device may include a plurality of second lumens, each of the first lumen and the plurality of second lumens being filled with a fluid during extruding the first layer, depositing the mesh layer, and extruding the second layer. The fluid may maintain patency of each of the first lumen and the second lumen during extruding the first layer, depositing the mesh layer, and extruding the second layer. The fluid may be a non-compressible liquid, such as water, a mixture of water and isopropyl alcohol, silicone fluid, or combination thereof. Alternatively, the fluid may be a pressurized gas, such as air, nitrogen, or combination thereof. The pressurized gas may have a first pressure during extruding the first layer and a second pressure during depositing the mesh layer and extruding the second layer, the second pressure being greater than the first pressure. The first layer of material may define the first and second lumens. Alternatively, the first lumen may be defined by a first tube and the second lumen may be defined by a second tube, the first layer of material being extruded over the first and second tubes, the first tube and the second tube each being composed of a different material than the first layer of material of the elongate body. Each of the first tube and the second tube may be composed of a material having a higher durometer than the first layer of material of the elongate body. For example, the second tube may be composed of at least one of polyimide, nylons, fluorinated ethylene propylene (FEP), and polyether ether ketone (PEEK). During the method, the elongate body is wound about a first spool after extruding a first layer of material to form an elongate body; the elongate body is transferred from the first spool to a second spool during depositing a mesh layer over the first layer of material; and the elongate body is transferred from the second spool to a third spool during extruding a second layer of material over the mesh layer.

A method of producing a multi-lumen medical device may include extruding a layer of a first material over a first lumen tube and at least one second lumen tube to form an elongate body having a length of at least 100 feet, a first lumen, and at least one second lumen; depositing a mesh layer over the layer of first material; extruding a layer of a second material over the mesh layer, each of the first lumen tube and the at least one second lumen tube at least one of: being composed of a third material that has a higher durometer than the first material; and containing a fluid therein. The first lumen may contain a removable solid core during extruding a layer of first material, depositing a mesh layer, and extruding a layer of second material, the solid core being removed after extruding a layer of second material. Each of the first lumen tube and the at least one second lumen tube may be composed of a third material that has a higher durometer than the first material. For example, the third material may be polyimide, nylons, fluorinated ethylene propylene (FEP), and/or polyether ether ketone (PEEK). Alternatively, each of the first lumen tube and the at least one second lumen tube may contain a pressurized gas having a first pressure during extruding a layer of a first material and having a second pressure during depositing a mesh layer over the layer of first material and extruding a layer of second material, the first pressure being less than the second pressure. The method may further include cutting the elongate body into a plurality of shortened elongate bodies, each shortened elongate body having a second length that is less than approximately six feet. The step of extruding a second layer of material may include extruding a second layer of material over the mesh layer in one or more sections such that the multi-lumen elongate body includes one or more sections of exposed mesh layer, the elongate body being cut in the sections of exposed mesh layer.

A system for producing a multi-lumen elongate body may include a first extruder configured to extrude a layer of first material to form an elongate body with a first lumen and a second lumen, the elongate body having a length of at least 100 feet; a machine configured to deposit a mesh layer over the layer of first material along the entire length of the elongate body; a second extruder configured to extrude a layer of second material over the mesh layer along at least a portion of the elongate body; and a source of fluid in fluid communication with the second lumen during extrusion of the layer of first material, deposition of the mesh layer over the layer of first material, and extrusion of the layer of second material over the mesh layer. The source of fluid may be a pressurized gas or a non-compressible liquid.

BRIEF DESCRIPTION OF THE DRAWINGS

A more complete understanding of the present invention, and the attendant advantages and features thereof, will be more readily understood by reference to the following detailed description when considered in conjunction with the accompanying drawings wherein.

DETAILED DESCRIPTION OF THE INVENTION

Figure 1:
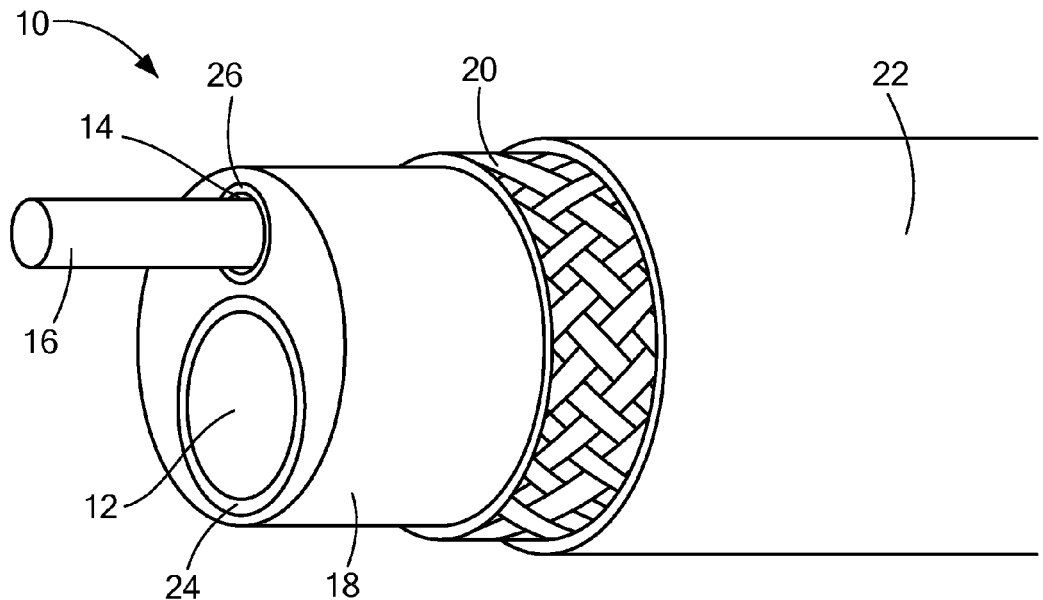
FIG. 1 shows a cutaway view of an exemplary multi-lumen medical device.

Referring now to FIG. 1, a cutaway view of an exemplary multi-lumen steerable catheter is shown. Although the methods and configurations shown and described herein may be used for, at least, steerable catheters and steerable sheaths, any type of multi-lumen device capable of being produced as shown and described here is referred to herein for simplicity as "steerable catheter," "catheter," or "elongate body." For example, the methods and configurations shown and described herein may be used for multi-lumen catheters or sheaths that are not steerable or have a plurality of minor lumens with fewer than all minor lumens housing a pull wire (such as catheters having one or more minor lumens for fluid injection or return, electrical connection to the console, housing sensors, or other non-pull wire uses). Also, although the individual layers of the steerable catheter are shown having difference lengths, it will be understood that this is for the sake of illustration only, and that all layers, including those not shown, may be coterminous. Of note, the device components have been represented where appropriate by conventional symbols in the drawings, showing only those specific details that are pertinent to understanding the embodiments of the present invention so as not to obscure the disclosure with details that will be readily apparent to those of ordinary skill in the art having the benefit of the description herein. Moreover, while certain embodiments or figures described herein may illustrate features not expressly indicated on other figures or embodiments, it is understood that the features and components of the penetration device disclosed herein may be included in a variety of different combinations or configurations without departing from the scope and spirit of the invention.

As shown in FIG. 1, a non-limiting example of a catheter 10 may include a major lumen 12 and one or more minor lumens 14. In use, the one or more minor lumens 14 may each contain a pull wire 16. The steerable catheter may be manufactured with several layers of material, such as an inner layer 18, a braided mesh middle layer 20, and an outer layer 22. However, it will be understood that more or fewer layers, and/or different layers than those shown in FIG. 1, may be used. Additionally, although a slight gap is shown between each layer for clarity, it will be understood that the layers may be in contact or substantially in contact with each other.

Before the finished catheter 10 is produced, the major 12 and minor 14 lumen may be each be a tube 24, 26 of material composed of, for example, polytetrafluoroethylene (PTFE). During the first pass of an extrusion process, each tube 24, 26 for the major 12 and minor 14 lumens may be coated with a layer of material to form the inner layer 18. In currently known devices, the major lumen tube 24 and the minor lumen tube 26 may be composed of PTFE. In the present invention, however, the minor lumen tube 26 may be a non-collapsible tube composed of a material having a higher durometer than PTFE, such as nylons, fluorinated ethylene propylene (FEP), polyether ether ketone (PEEK), ethylene tetrafluoroethylene (ETFE), or combinations thereof. In either case, the inner layer 18 may be composed of the same material as the major lumen tube 24, for example, PTFE, which may help the device maintain flexibility. After the inner layer is deposited over the major lumen tube 24 and the minor lumen tube 26, the inner layer may be substantially circular in cross section. Alternatively, the inner layer may be extruded to have any desired shape, including those that are not circular in cross section.

After the first pass of extrusion is finished, the inner layer 18 may be covered in a layer of braided mesh 20. This braided mesh middle layer 20 may be braided, coiled, or woven about the inner layer 18 using a plurality of individual wires or threads, which may be composed of, for example, stainless steel. Alternatively, the braided mesh 20 may be pre-woven and placed about the inner layer 18 as a sheet or sheath. However, depending on the type and number of layers used, desired configuration, and/or intended use, the braided mesh layer 20 may be at a different location, overlayed on the inner layer 18 in a different manner, and/or may have a configuration other than a braided or woven mesh.

Figure 2:
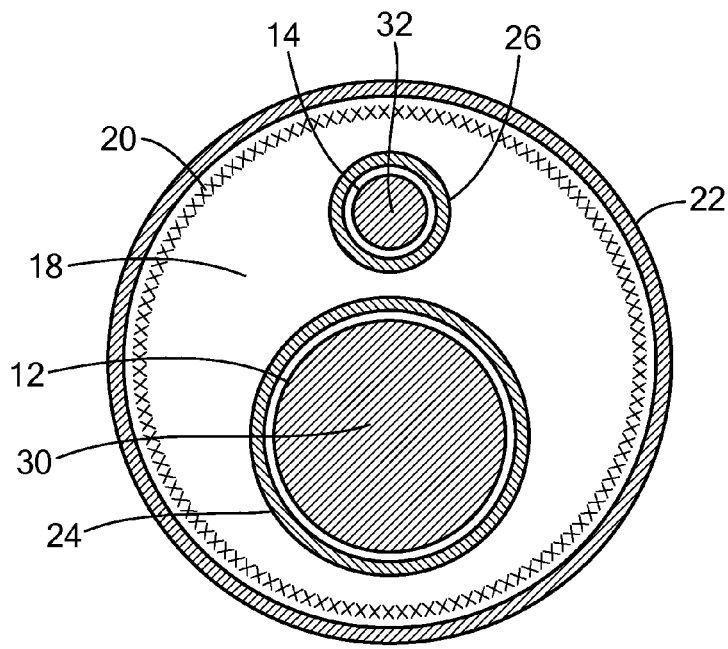
FIG. 2 shows a cross-sectional view of a multi-lumen medical device with mandrels inserted into the major and minor lumens during prior art manufacturing methods.

Referring now to FIG. 2, a cross-sectional view of a multi-lumen steerable catheter during prior art manufacturing methods is shown. Extrusion methods may be used to produce the catheter, as discussed in FIG. 1. However, currently known methods of producing a catheter having one or more minor lumens involve the use of a mandrel in each lumen to ensure that the lumens remain open during the entire process. As shown in FIG. 2, for example, a mandrel 30 is disposed within the major lumen 12 and a mandrel 32 is disposed within each minor lumen 14. Although a small gap is shown between the mandrels 30, 32 and the lumen tubes 24, 26 in FIG. 2 for illustration purposes only, it will be understood that the mandrels 30, 32 will be at least substantially in contact with the inner surfaces of the lumen tubes 24, 26 during the manufacturing process, with no or very little gap present. The mandrels may be passed through the extruder in the first pass for each length of catheter body, so that the inner layer 18 is extruded around the mandrels. For example, this may be used if the catheter 10 is extruded such that the major 12 and minor 14 lumens are defined by the inner layer 18, rather than by individual tubes 24, 26 about which the inner layer 18 is extruded. Alternatively, such as when tubes 24, 26 are used, the mandrels may be disposed within the major lumen tube 24 and the minor lumen tube 26 prior to the first pass extrusion, in order to support the tubes during the first pass, mesh overlay, and second pass. After the extrusion process is complete, the mandrels 30, 32 are removed. This is in contrast to the current invention, in which cores are not required to preserve patency of the minor lumens 14 during manufacture, such as during extrusion and mesh layer overlay.

Figure 3:
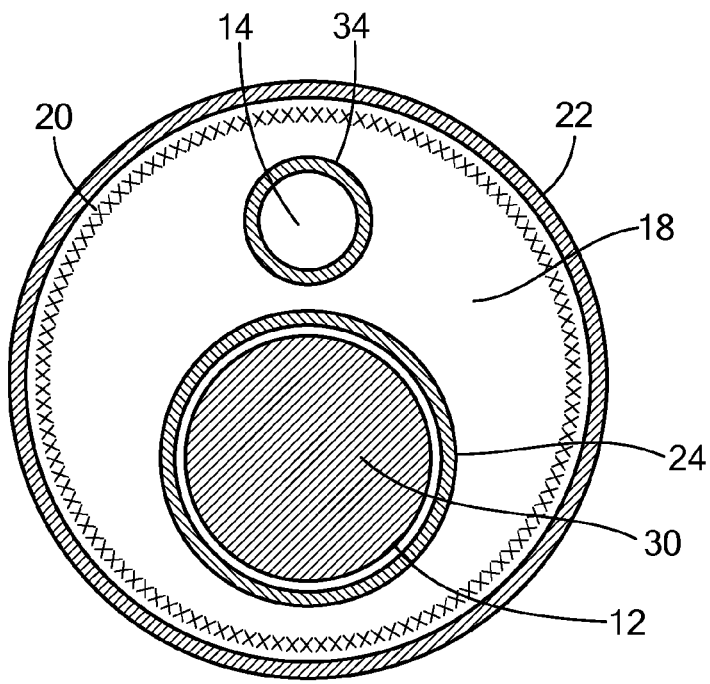
FIG. 3 shows a cross-sectional view of a multi-lumen medical device with a mandrel inserted into the major lumen during manufacturing, the multi-lumen medical device having a minor lumen composed of a non-collapsible material.
Figure 4:
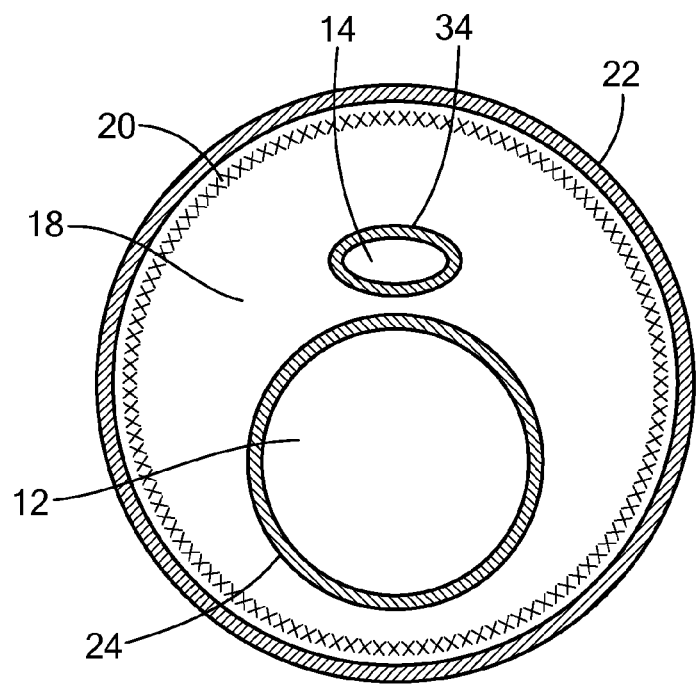
FIG. 4 shows a cross-sectional view of a multi-lumen medical device having a non-round minor lumen composed of a non-collapsible material.
Figure 5:
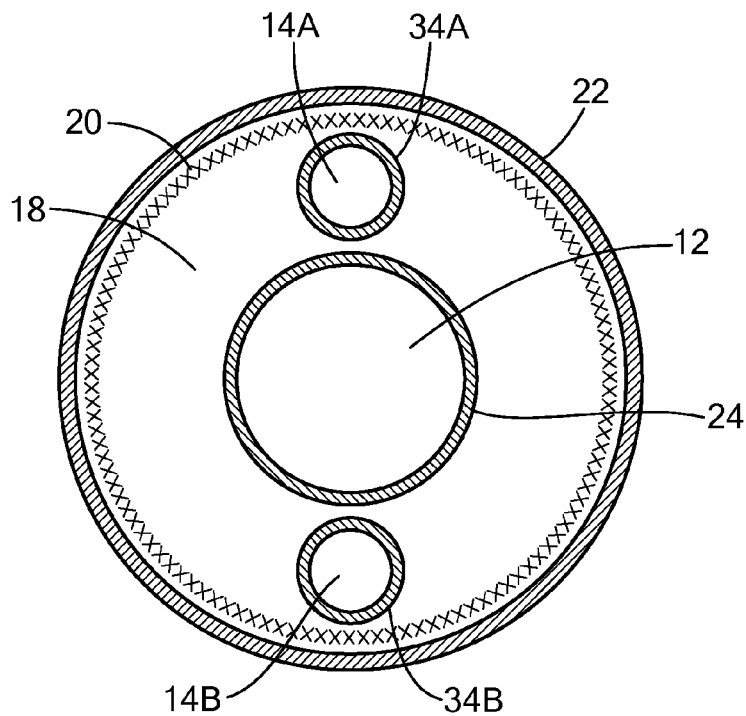
FIG. 5 shows a cross-sectional view of a multi-lumen medical device having two minor lumens composed of a non-collapsible material.
Figure 6:
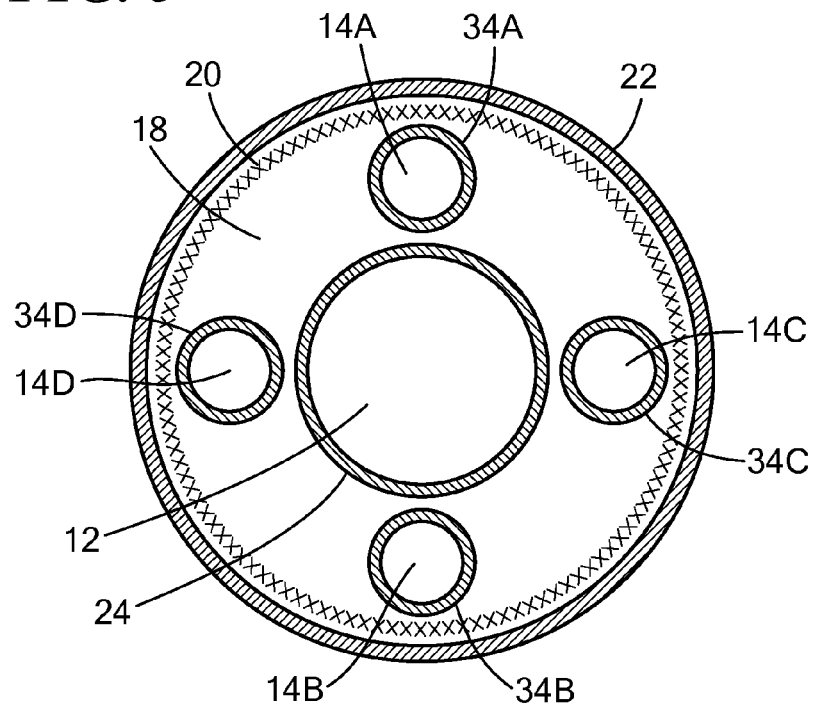
FIG. 6 shows a cross-section view of a multi-lumen medical device having a plurality of minor lumens composed of a non-collapsible material.

Referring now to FIGS. 3-6, cross-sectional views of multi-lumen medical devices are shown, the devices having one or more minor lumens composed of a non-collapsible material. For example, the device may be a catheter. Unlike the currently known catheter shown in FIG. 2, the multi-lumen catheter of FIGS. 3-6 are manufactured using one or more minor lumens 14 each defined by a minor lumen tube 34 that is composed of a material having a higher durometer than PTFE. For example, the minor lumen tubes 34 may be composed of polyimide, nylons, fluorinated ethylene propylene (FEP), polyether ether ketone (PEEK), ethylene tetrafluoroethylene (ETFE), or combinations thereof. The more rigid minor lumen tubes 34 may enable the minor lumens to remain open, that is, not collapse, without a mandrel 32 being disposed within during the manufacturing process. This makes production more cost efficient because the cost of the mandrels are saved, makes production less labor intensive, and makes the product less susceptible to human error and damage. Although a small gap is shown between the mandrel 30 and the major lumen tube 24 in FIG. 3 for illustration purposes only, it will be understood that the mandrel 30 will be at least substantially in contact with the inner surfaces of the lumen tube 24 during the manufacturing process, with no or very little gap present. Alternatively, the major lumen tube 24 may also be composed of a non-collapsible material, like the one or more minor lumen tubes 34, that obviates the need for the mandrel 30 to maintain patency of the major lumen 12 during manufacture (as shown in FIGS. 4-6). Although a mandrel 30 is shown in only some figures, it will be understood that a mandrel 30 may or may not be used in the major lumen 12 of any of the configurations shown and described herein.

The catheter 10 shown in FIG. 3 includes a single minor lumen 14 having a substantially circular cross section. FIG. 4 shows a non-limiting example of a minor lumen 14 having a non-circular cross section. Although the minor lumen 14 in FIG. 4 is shown as being substantially ellipsoidal, it will be understood that the minor lumen 14 can have any cross-sectional shape sufficient to house fluid, a pull wire, electrical wires, sensors, or other component. Non-circular minor lumen cross sections may be impractical or impossible in currently catheters and methods of production that require the use of a mandrel in each minor lumen 14. By eliminating the need to use a mandrel, the non-collapsible minor lumen tube 34 may make any of a variety of minor lumen cross sections possible. FIG. 5 shows an exemplary embodiment having two minor lumens 14A, 14B each defined by a non-collapsible tube 34A, 34B, respectively, and FIG. 6 shows an exemplary embodiment having four minor lumens 14A, 14B, 14C, 14D each defined by a non-collapsible lumen 34A, 34B, 234C, 34D, respectively. Further multi-lumen embodiments having one or more non-collapsible minor lumen tubes 34 are possible and contemplated other than those shown and described herein.

Referring now to FIGS. 7A-10, cross-sectional views of multi-lumen catheters are shown, the catheters having one or more minor lumens, the one or more minor lumens containing a non-compressible liquid or pressurized gas. Like the multi-lumen catheters shown in FIGS. 3-6, the multi-lumen catheters shown in FIGS. 7A-10 do not require a mandrel to preserve patency of the minor lumens 14 during manufacture, including during extrusion and mesh layer overlay, which may offer the advantages discussed regarding FIGS. 3-6. Although the minor lumens 14 in FIGS. 7A-10 may be defined by tubes 36 composed of a non-collapsible material such as polyimide, nylons, fluorinated ethylene propylene (FEP), polyether ether ketone (PEEK), ethylene tetrafluoroethylene (ETFE), or combinations thereof, the tubes 36 may alternatively be composed of PTFE or other suitable material. Alternatively, the minor lumens 14 may not be defined by a tube (as shown, for example, in FIGS. 7A and 8-10), but may instead be extruded such that they are defined by the inner layer itself 18 (as shown, for example, in FIG. 7B). Although a small gap is shown between the mandrel 30 and the lumen tube 24 in FIG. 8 for illustration purposes only, it will be understood that the mandrel 30 will be at least substantially in contact with the inner surfaces of the lumen tube 24, or the portion of the inner layer 18 defining the major lumen 12, during the manufacturing process, with no or very little gap present, if a mandrel 30 is used. Alternatively, the major lumen tube 24 may also contain a non-compressible liquid or pressurized gas, like the one or more minor lumen tubes 36, that obviates the need for the mandrel 30 to maintain patency of the major lumen 12 during manufacture (as shown in FIGS. 7A, 7B, 9, and 10). Although a mandrel 30 is shown in only some figures, it will be understood that a mandrel 30 may or may not be used in the major lumen 12 of any of the configurations shown and described herein.

Figure 14A:
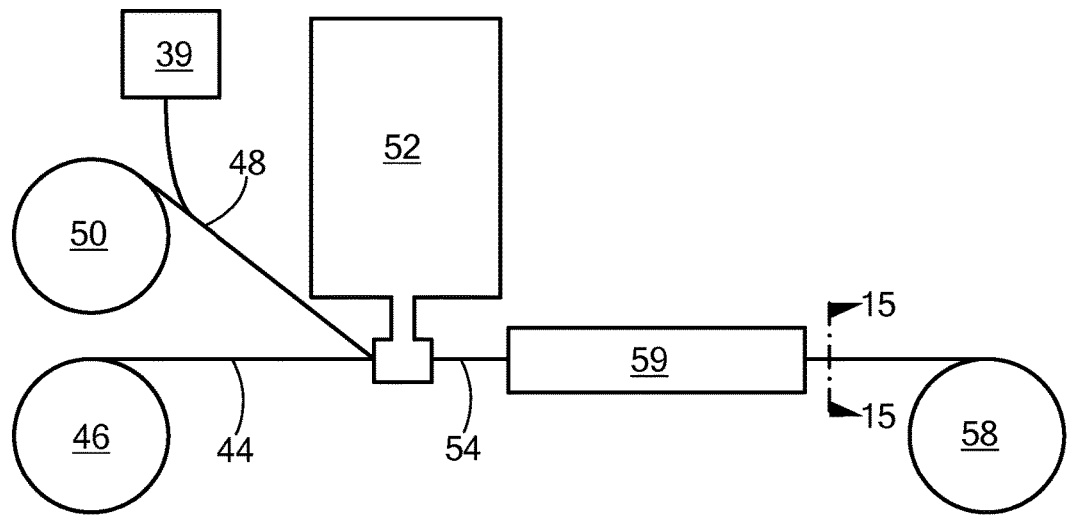
FIG. 14A shows a schematic view of a first step in a continuous extrusion multi-lumen medical device manufacturing process.
Figure 14B:
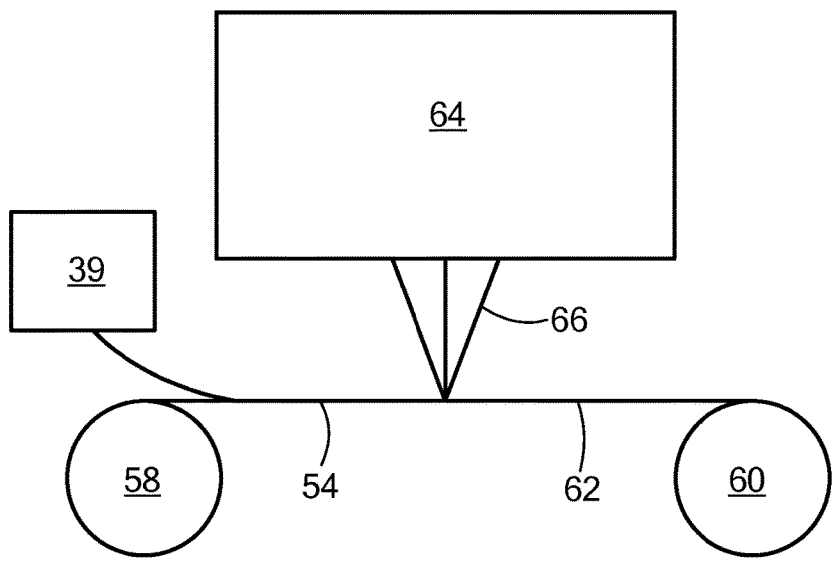
FIG. 14B shows a schematic view of a second step in a continuous extrusion multi-lumen medical device manufacturing process.
Figure 14C:
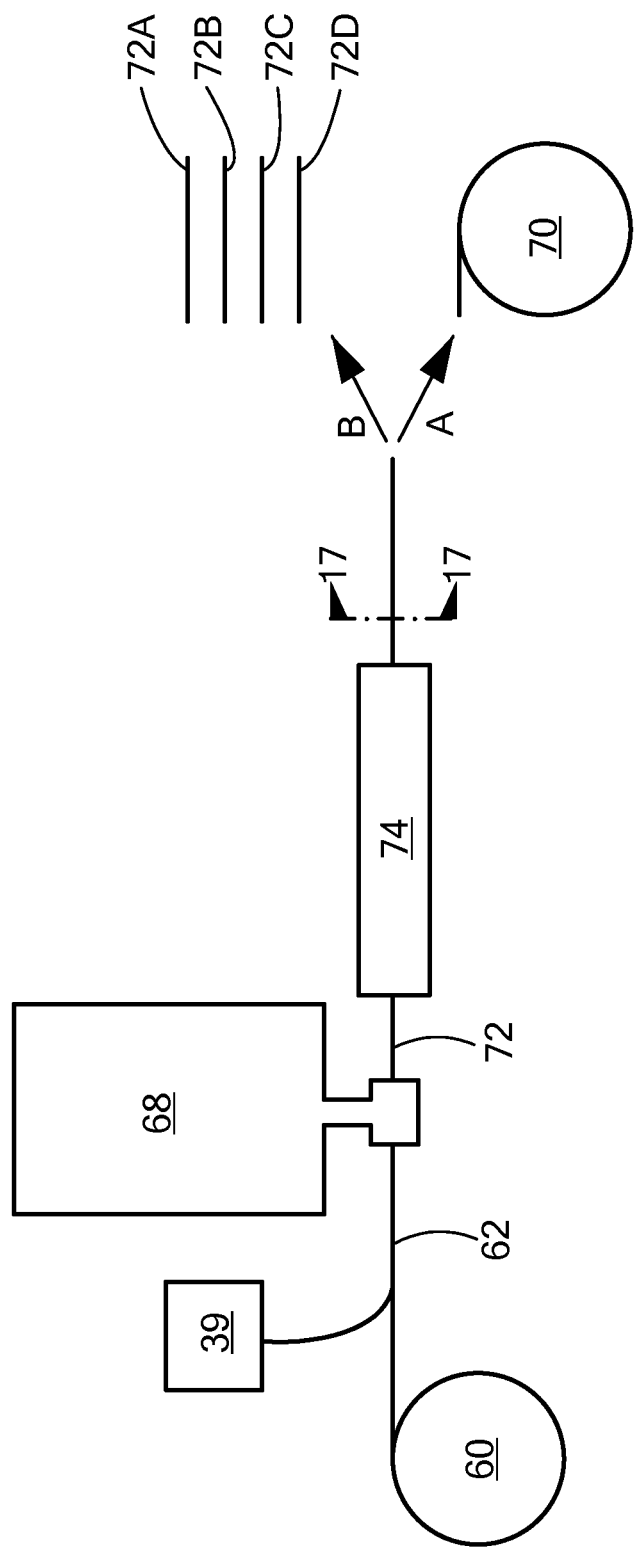
FIG. 14C shows a schematic view of a third step in a continuous extrusion multi-lumen medical device manufacturing process.

In order to preserve patency of the major lumen 12 and/or minor lumens 14 during manufacture, the lumens 12, 14 may be filled with a non-compressible fluid and/or a pressurized gas. The fluid within the lumens 12, 14 in FIGS. 7A-10 are collectively referred to with the number "38" and the term "fluid core." For example, the minor lumens 14 and/or major lumen 12 may be filled with a fluid core 38 of water, a combination of water and isopropyl alcohol, air (for example, atmospheric air such as a combination of at least oxygen and nitrogen, and optionally also including gases such as argon and carbon dioxide), nitrogen, silicone fluid, or combinations thereof. Other non-compressible fluids and/or gases may also be used. If a gaseous fluid core 38 is used, the pressure of the gas may be adjusted at different stages in the manufacturing process. For example, the minor lumens 14 and/or major lumen 12 may be filled with a fluid core 38 of compressed air at a first pressure during the first extrusion pass. A relatively low pressure within the lumens 12, 14 may be used during the first pass because there may be little to no external pressure exerted on the lumens 12, 14 that would require substantial pressure within the lumens 12, 14 in order to maintain patency. During subsequent stages such as mesh layer overlay and a second extrusion pass, however, the pressure of the gas within the lumens may be increased to a pressure sufficient to withstand the external pressure exerted as, for example, the mesh layer is overlayed on the inner layer 18 and the outer layer, such as a thermoplastic, is extruded over the mesh layer. Further, the pressure should be such that the internal pressure does not cause rupture or damage to the lumens 12, 14. The lumens 12, 14 may be in fluid communication with a source of fluid 39 during production (as shown in FIGS. 14A-14C). As a non-limiting example, the fluid source may contain a pressurized gas during each stage of production, with the pressure being adjusted to the desired pressure for each step. Alternatively, the lumens 12, 14 may be in fluid communication with a first source of pressurized air during the first pass extrusion, and in fluid communication with a second source of pressurized air during the mesh overlay step and the second pass extrusion, the second source of pressurized air being at a higher pressure than the first source of pressurized air. As the manufacturing process may include additional steps that likewise exert pressure on the lumens 12, 14, the increased pressure of the gas within the lumens 12, 14 may preserve patency of the lumens 12, 14 during these steps as well.

Figure 7A:
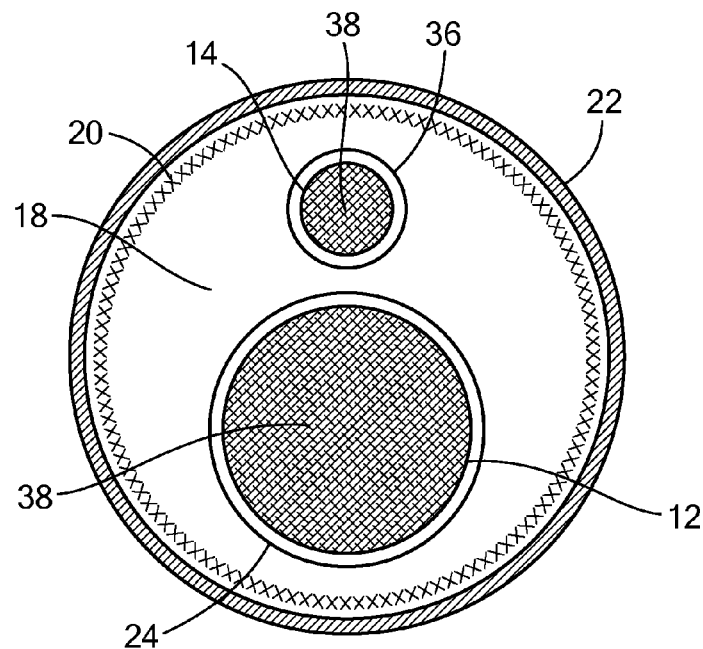
FIG. 7A shows a cross-sectional view of a multi-lumen medical device having a minor lumen and a major lumen having non-compressible liquid or pressurized gas within, with the major and minor lumens each being defined by a lumen tube.
Figure 7B:
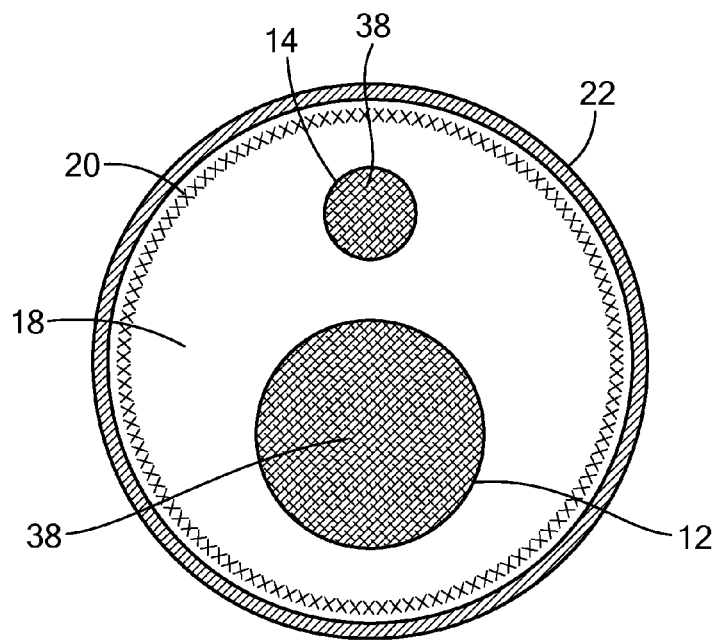
FIG. 7B shows a cross-sectional view of a multi-lumen medical device having a minor lumen and a major lumen having non-compressible liquid or pressurized gas within, with the major and minor lumens each being defined by the inner layer.
Figure 8:
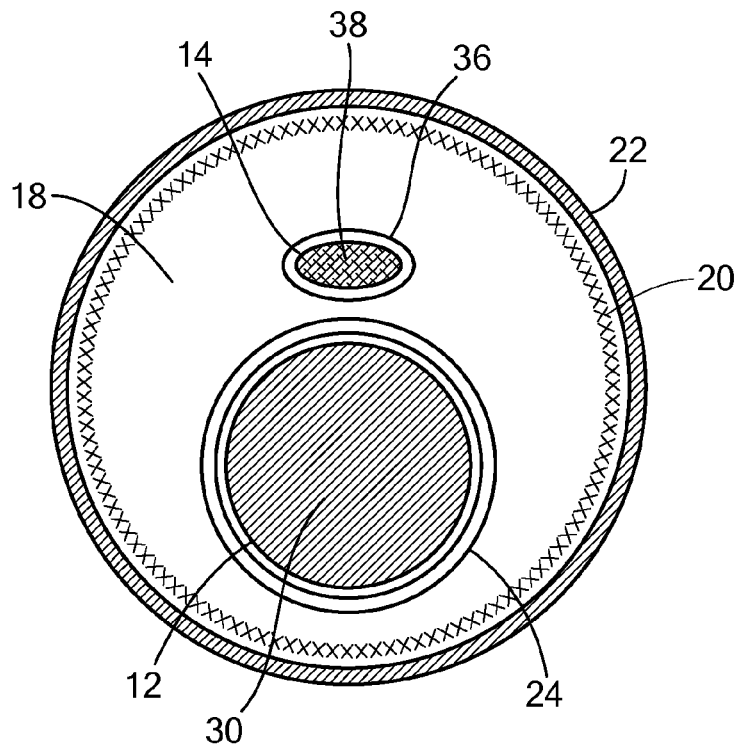
FIG. 8 shows a cross-sectional view of a multi-lumen medical device with mandrel inserted into the major lumen during manufacturing, the multi-lumen medical device having a non-round minor lumen with non-compressible liquid or pressurized gas within.

The catheter 10 shown in FIGS. 7A and 7B includes a single minor lumen 14 having a substantially circular cross section. Additionally, use of a fluid core 38 of non-compressible fluid or pressurized gas instead of a rigid mandrel in the lumens may allow for the use of any of a variety of minor lumen cross sections, other than just circular or substantially circular, because the fluid flows into and offers support for any shape. FIG. 8 shows an exemplary embodiment having a minor lumen 14 with a non-circular cross-sectional shape. Although the minor lumen 14 in FIG. 8 is shown as being substantially ellipsoidal, it will be understood that the minor lumen 14, or the major lumen 12, can have any cross-sectional shape sufficient to house fluid, a pull wire, electrical wires, sensors, or other component. Non-circular minor lumen cross sections may be impractical or impossible in currently catheters and methods of production that require the use of a mandrel in each lumen 12, 14. By eliminating the need to use a mandrel, the fluid core 38 may make any of a variety of lumen cross sections possible.

Figure 9:
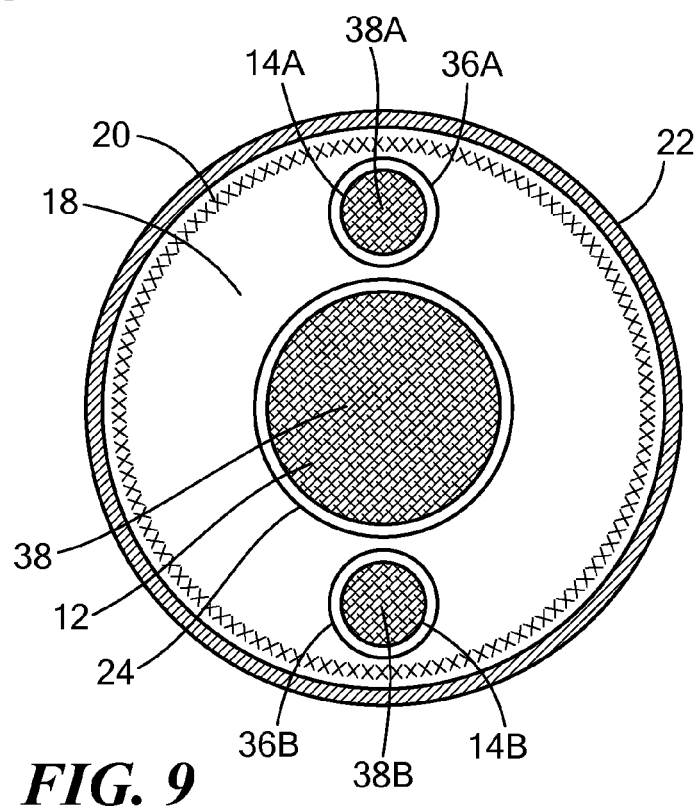
FIG. 9 shows a cross-sectional view of a multi-lumen medical device having a major lumen and two minor lumens with non-compressible liquid or pressurized gas within.
Figure 10:
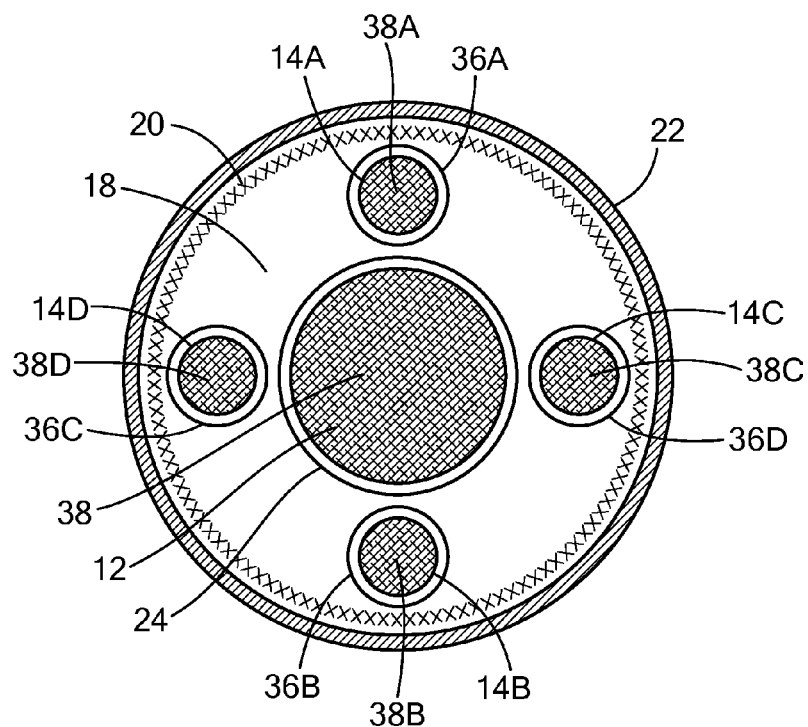
FIG. 10 shows a cross-sectional view of a multi-lumen medical device having a major lumen and a plurality of minor lumens with non-compressible liquid or pressurized gas within.

FIG. 9 shows an exemplary embodiment having two minor lumens 14A, 14B each defined by a non-collapsible tube 34A, 34B, respectively, and FIG. 10 shows an exemplary embodiment having four minor lumens 14A, 14B, 14C, 14D each defined by a non-collapsible lumen 34A, 34B, 234C, 34D, respectively. Further multi-lumen embodiments having one or more non-collapsible minor lumen tubes 34 are possible and contemplated other than those shown and described herein. In this embodiment, the fluid source 39 in fluid communication with the lumens 12, 14 shown in FIGS. 14A-14C may contain a non-compressible liquid.

Figure 11:
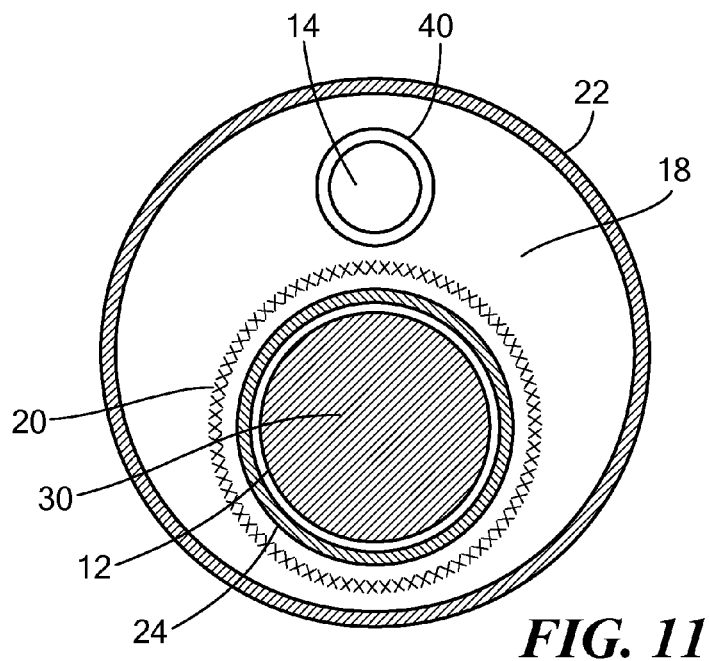
FIG. 11 shows a cross-sectional view of a multi-lumen medical device in which a minor lumen is disposed between a braided mesh layer and an outer thermoplastic layer.
Figure 12:
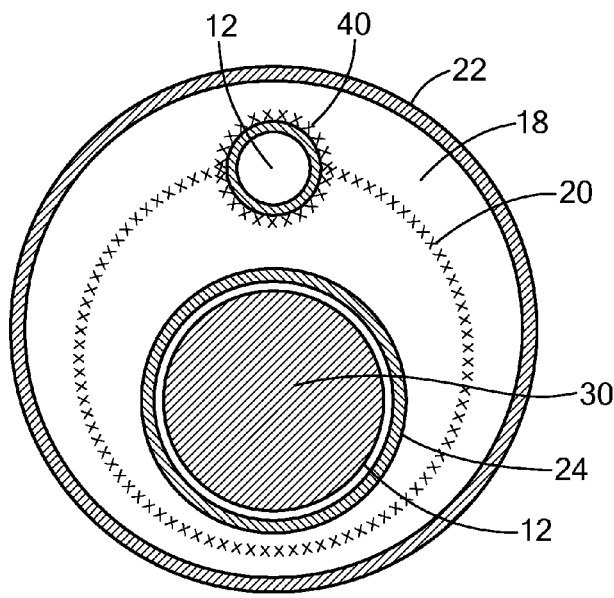
FIG. 12 shows a cross-sectional view of a multi-lumen medical device in which a minor lumen is disposed within the matrix of a braided mesh layer.
Figure 13:
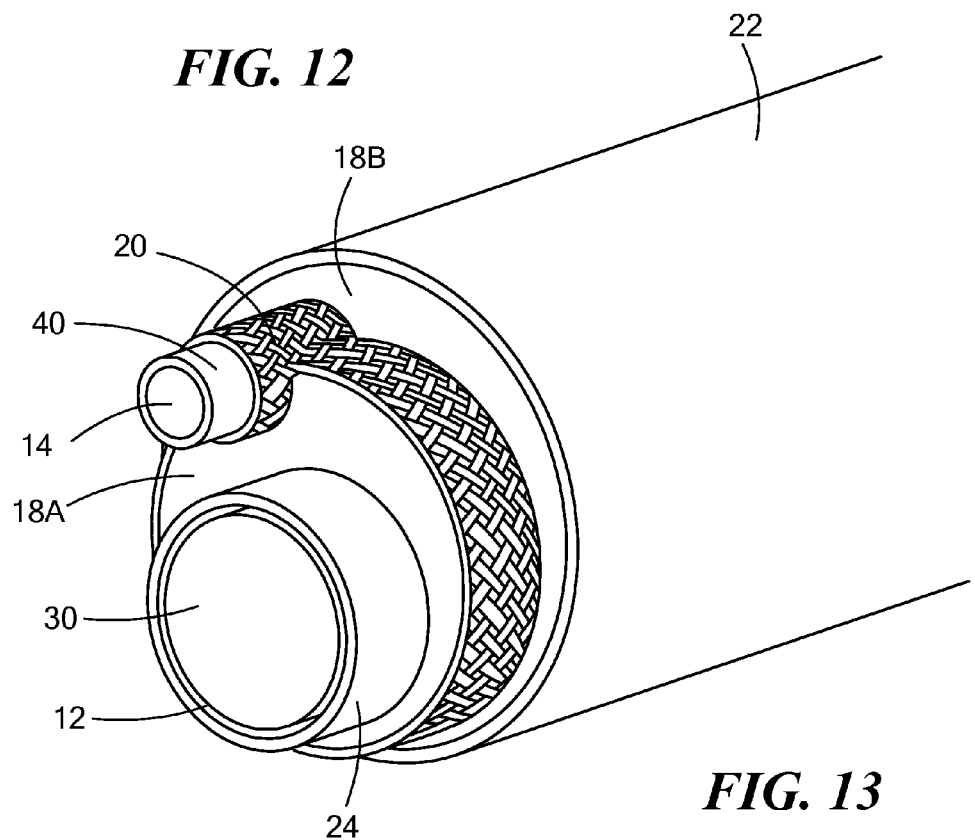
FIG. 13 shows a cutaway view of the multi-lumen medical device in which the minor lumen is disposed within the matrix of a braided mesh layer.

Referring now to FIGS. 11-13, cross-sectional views of two exemplary multi-lumen catheters are shown. The minor lumens 14 in FIGS. 3-10 are shown as being located beneath the mesh layer 20; however, the minor lumens 14 may alternatively be placed in other locations. In the non-limiting embodiment shown in FIG. 11, the minor lumen 14 may be located on the outside of the mesh layer 20, between the mesh layer 20 and the outer layer 22. During manufacture, the major lumen 12 may be formed by covering the major lumen tube 24 with an inner layer 18 during a first pass extrusion, and then the mesh layer 20 may be overlaid on the inner layer 18. As shown and described in FIGS. 3-10, a mandrel 30 may or may not be used in the major lumen 12. After the mesh layer 20 is in place, a minor lumen tube 40 may be added on top of the mesh layer 20 and passed through a second extrusion pass, creating the outer layer 22 over the mesh layer 20 and minor lumen 14. In the non-limiting embodiment shown in FIGS. 12 and 13, the minor lumen 14 may be part of the mesh layer 20. For example, the major lumen tube 24 may be covered with a first inner layer 18A during a first pass extrusion, and then the minor lumen tube 40 may be interwoven with (for example, being passed through the openings in the braid, weave, or mesh pattern) or covered in a layer of mesh 20 that is also interwoven with the layer of mesh 20 surrounding the first inner layer 18A. The elongate body may then be passed through a second extrusion pass, which may add more of the inner layer material in a second inner layer 18B on top of the mesh layer 20, and a third extrusion pass, which may create the outer layer 22 over the mesh layer 20 and/or second inner layer 18B and minor lumen tube 40. Alternatively, the minor lumens 14 may be included in other configurations than those shown and described in FIGS. 3-13. Although a small gap is shown between the mandrel 30 and the lumen tube 24 in FIGS. 11-13 for illustration purposes only, it will be understood that the mandrel 30 will be at least substantially in contact with the inner surfaces of the lumen tube 24 during the manufacturing process, with no or very little gap present.

Referring now to FIGS. 14A-17, a schematic view of a three-step continuous extrusion process is shown. Although manufacturing a steerable (or non-steerable) multi-lumen catheter 10 may involve more than three steps, FIG. 14 shows a process including a first extrusion pass, a mesh layer overlay, and a second extrusion pass for illustration. As discussed in the Background section, currently known manufacturing processes for multi-lumen devices involve manufacturing a usable length at a time. For example, for use in a medical device including an 86.4 cm multi-lumen catheter body for intravascular use, each approximately 86.4-cm length of catheter body may be manufactured individually, which each length undergoing, for example, a first extrusion pass, an overlay step, and a second extrusion pass. In FIG. 14, however, a more efficient method is shown, in which the first and second extrusion passes and the mesh overlay step may each be performed continuously for a length of product that is longer than a typical usable length. That is, a catheter body length of, for example, approximately 100 to approximately 5000 feet may undergo each step at a time, rather than each usable length at a time, and the finished length may then be cut to a desired length. Additionally, the methods shown and described herein maintain patency, or prevent collapse, of the lumens during manufacturing processes that include more than one step, including extrusion.

Figure 15:
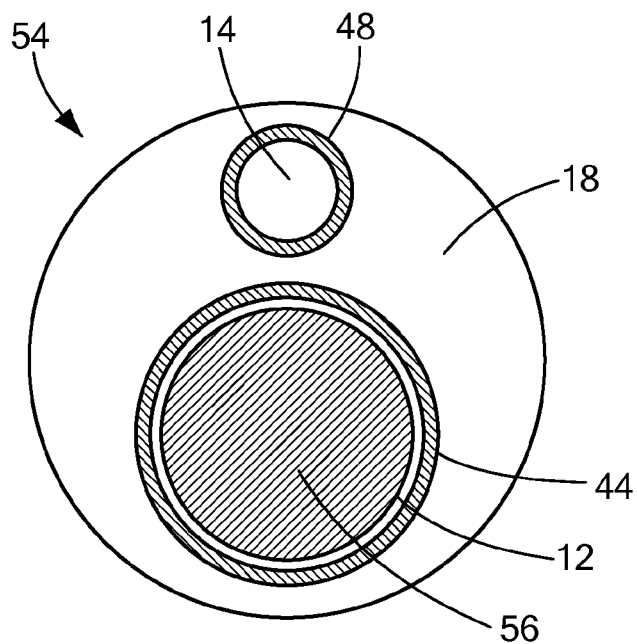
FIG. 15 shows a cross-sectional view of an unfinished multi-lumen medical device body after the first step of the continuous extrusion process.

In the non-limiting process shown in FIGS. 14A-14C, a length of major lumen tubing 44 contained on a first spool 46 and at least one length of minor lumen tubing 48 contained on a second spool 50 may be passed through an extruder 52 in a first extrusion pass. During the first extrusion pass shown in FIG. 14A, an inner layer 18 composed of, for example, PTFE or other suitable biocompatible material, may be deposited over the major lumen tubing 44 and at least one minor lumen tubing 48. This first pass may create a length (for example, between approximately 100 to approximately 5000 feet) of unfinished catheter body 54 that includes the major lumen 12, at least one minor lumen 14, and the inner layer 18 (as shown in FIG. 15).

The major lumen tubing 44 and the minor lumen tubing 48 may each be composed of a commonly used material such as PTFE, or at least the one or more minor lumen tubing 48 and major lumen tubing 24 may be composed of a non-collapsible material such as polyimide, nylons, fluorinated ethylene propylene (FEP), polyether ether ketone (PEEK), ethylene tetrafluoroethylene (ETFE), or combinations thereof, as shown and described in FIGS. 3-6. Alternatively, the first pass extrusion may produce an unfinished catheter body 54 that includes the inner layer 18, with the inner layer 18 defining both the major lumen 12 and the at least one minor lumen 14. In either configuration, the at least one minor lumen 14 and/or the major lumen 12 may be filled with a non-compressible fluid or a pressurized gas. For example, the at least one minor lumen 14 and/or the major lumen 12 may be in fluid communication with a source of fluid 39, such as a source of pressurized gas or a source of non-compressible liquid, during each step of the manufacturing process. Alternatively, the major lumen 12 and/or at least one minor lumen 14 may contain a core material 56 that preserves patency of the lumens 12, 14 during the manufacturing process. For example, the core material may be composed of metal, such as silver-plated copper. The unfinished catheter body 54 may be wound about a third spool 58 after passing through the first pass extruder 52. If it is desired to produce a catheter 10 similar to that shown in FIG. 11, in which a minor lumen 14 is located outside the mesh layer 20, or in FIGS. 12 and 13, in which a minor lumen 14 passes through the weave or braid of the mesh layer 20, only the major lumen tubing 44 may be passed through the first extruder 52, with the minor lumen tubing 48 being added in subsequent steps.

After the inner layer 18 is extruded over the major lumen tubing 44 and the at least one minor lumen tubing 48, the unfinished catheter body 54 may be passed through a water bath 59 to cool the inner layer material before the unfinished catheter body 54 is wound about the third spool 58. The third spool 58 may then be transferred to, or remain in, a suitable location for the mesh overlay step.

Figure 16:
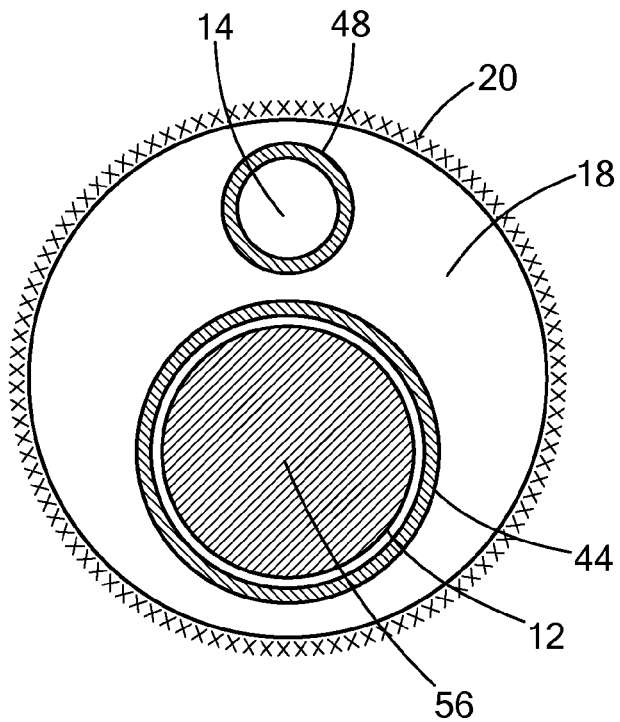
FIG. 16 shows a cross-sectional view of an unfinished multi-lumen medical device body after the second step of the continuous extrusion process.

Once in a suitable location for the mesh overlay step shown in FIG. 14B, the unfinished catheter body 54 may be passed from the third spool 58 to a fourth spool 60. As the unfinished catheter body 54 is passed from the third spool 58 to the fourth spool 60, the mesh layer may be overlayed on the length of the inner layer 18, or individual wires or threads (which may be composed of, for example, stainless steel) may be braided, coiled, or woven about the inner layer 18, producing a length of intermediate unfinished catheter body 62 that includes the major lumen 12, at least one minor lumen 14, an inner layer 18, and a mesh layer 20 (as shown in FIG. 16). This intermediate unfinished catheter body 62 may have the same length as the unfinished catheter body 54, for example, between approximately 100 feet and approximately 5000 feet. If it is desired to produce a catheter 10 similar to that shown in FIGS. 12 and 13, in which a minor lumen 14 passes through the weave or braid of the mesh layer 20, at least one length of minor lumen tubing 48 may be placed proximate the unfinished product 54 as a weaving machine 64 weaves the mesh wires or threads 66 about the at least one minor lumen tubing 48, so as to weave the at least one minor lumen tubing 48 into the mesh layer 20. Alternatively, the at least one length of minor lumen tubing 48 may be woven into the mesh layer 20 in a separate process, and the mesh layer 20 with integrated one or more minor lumens 14 may be overlayed on the unfinished product 54 in a sheet. Also, although not shown, it is contemplated that at least one length of minor lumen tubing 48 may be placed proximate the unfinished product beneath the mesh layer during the mesh overlay step, rather than placing the at least one length of minor lumen tubing 48 proximate the major lumen tubing 44 during the first extrusion pass. That is, the at least one minor lumen 14 may be created during the first extrusion pass or the mesh overlay step.

Figure 17:
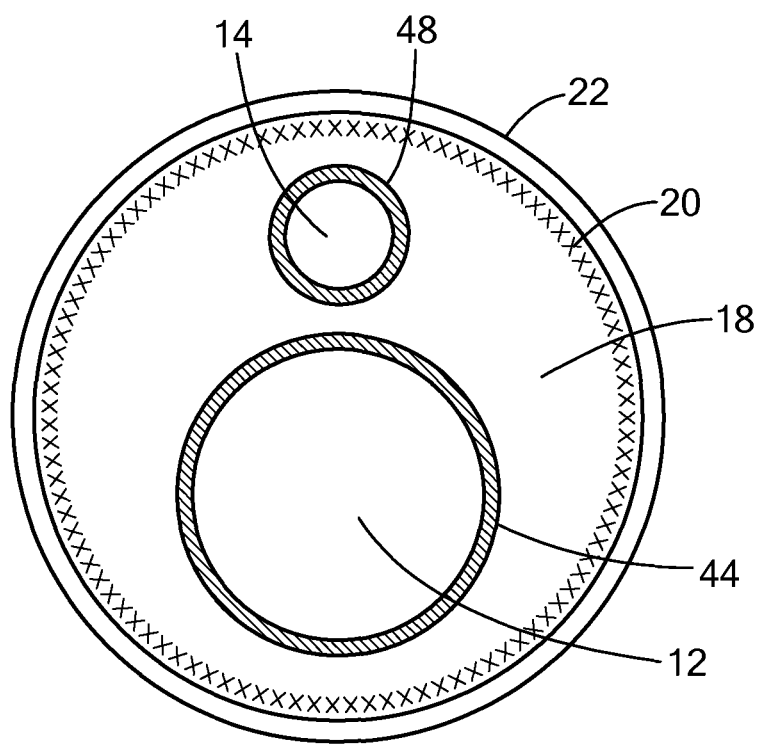
FIG. 17 shows a cross-sectional view of a finished multi-lumen medical device body after the third step of the continuous extrusion process.

After the mesh overlay step, the intermediate unfinished catheter body 62 may be passed from the fourth spool 60 through a second extruder 68 and, optionally, onto a fifth spool 70, in a second extrusion pass shown in FIG. 14C. Alternatively, the intermediate unfinished catheter body 62 may be passed through the first extruder 52 in a second extrusion pass. During the second extrusion pass, an outer layer 22 composed of, for example, a thermoplastic or other suitable biocompatible material, may be extruded over the intermediate unfinished catheter body 62. This second pass may create a length of finished catheter body 72 that is the same length as in the first pass and mesh overlay step. For example, the length may be between approximately 100 feet and approximately 5000 feet. Further, the finished catheter body 72 may include a major lumen 12, at least one minor lumen 14, an inner layer 18, a mesh layer 20, and an outer layer 22 (as shown in FIG. 17). Optionally, the outer layer 22 may not be added to the entire length of the intermediate unfinished catheter body 62. Rather, a distal portion of the intermediate unfinished catheter body 62 may have an exposed area of mesh layer 20 that is not covered by the outer layer 22. In another option, the outer layer 22 may be extruded over the intermediate unfinished catheter body 62 in sections. For example, the outer layer 22 may be extruded in discrete sections of approximately 3.5 feet, with a section of approximately 0.5 foot (approximately six inches) of exposed mesh layer 20. That is, the second extrusion pass may produce a length of finished catheter body 72 that includes discrete sections in which the outer layer 22 is not deposited. This may be accomplished by, for example, switching the extruder between an on mode, in which material is deposited on the catheter body, and an off mode, in which material is not deposited on the catheter body as the intermediate unfinished catheter body 62 passes through the extruder. Once the second extrusion pass is complete, the finished catheter body 72 may be cut in the exposed mesh sections into usable lengths, with each end of each usable length having an exposed portion of mesh layer or a portion having no outer layer 22. These end portions may facilitate various finishing steps, such as balloon attachment, pull wire insertion, electrode attachment, and the like. In contrast to the present invention, currently known methods necessitate an additional step of removing the outer layer 22 in the catheter body usable length end portions in order to finish the device.

If it is desired to produce a catheter similar to that shown in FIG. 11, in which a minor lumen 14 is located outside the mesh layer 20, at least one length of minor lumen tubing 48 may be placed proximate the intermediate unfinished catheter body 62 and passed through the first 52 or second 68 extruder in the second extrusion pass, and the outer layer 22 may be extruded over the at least one minor lumen tubing 48 and intermediate unfinished catheter body 62. The finished catheter body 72 may be passed through a water bath 74 to cool the finished catheter body 72 before it is wound about the fifth spool 70 (as shown in path A in FIG. 14C). Alternatively, instead of being wound about the fifth spool 70, the finished catheter body 72 may be cut into one or more shorter lengths (as shown in path B in FIG. 14C). As a non-limiting example, the finished catheter body 72 may be cut into a plurality of shorter catheter bodies 72A, 72B, 72C, 72D, etc., each having a desired usable length (for example, approximately six feet or less).

As the finished catheter body 72 exits the water bath 74, it may be wound about the fifth spool 70 for storage, shipping, transportation, or sale, and each desired usable length of catheter body 72 may be cut from the length wound about the spool 70. Alternatively, the finished catheter body 72 may be cut into usable lengths immediately upon exiting the second extrusion pass. The core material 56, if used, may be removed from the major lumen 12 either before or after the finished catheter body 72 is cut into usable lengths. Likewise, additional components such as pull wires and/or distal polymer segments may be added either before or after the finished catheter body 72 is cut into usable lengths.

It will be appreciated by persons skilled in the art that the present invention is not limited to what has been particularly shown and described herein above. In addition, unless mention was made above to the contrary, it should be noted that all of the accompanying drawings are not to scale. A variety of modifications and variations are possible in light of the above teachings without departing from the scope and spirit of the invention, which is limited only by the following claims.

What is claimed is:

1. A method for producing a multi-lumen elongate body, the method comprising:
   extruding a first layer of material to form an elongate body with a first lumen and a second lumen, the elongate body having a length of at least 100 feet;
   depositing a mesh layer over the first layer of material along the entire length of the elongate body; and
   extruding a second layer of material over the mesh layer along at least a portion of the length of the elongate body.

2. The method of claim 1, wherein the length of at least 100 feet is a first length, the method further comprising cutting the elongate body into a plurality of shortened elongate bodies, each shortened elongate body having a second length that is less than the first length.

3. The method of claim 2, wherein the second length is less than approximately six feet.

4. The method of claim 2, wherein each of the first lumen and the second lumen is filled with a fluid during extruding the first layer, depositing the mesh layer, and extruding the second layer.

5. The method of claim 4, wherein the device includes a plurality of second lumens, each of the first lumen and the plurality of second lumens being filled with a fluid during extruding the first layer, depositing the mesh layer, and extruding the second layer.

6. The method of claim 4, wherein the fluid maintains patency of each of the first lumen and the second lumen during extruding the first layer, depositing the mesh layer, and extruding the second layer.

7. The method of claim 6, wherein the fluid is a non-compressible liquid.

8. The method of claim 7, wherein the non-compressible liquid is ones of water, a mixture of water and isopropyl alcohol, silicone fluid, or combination thereof.

9. The method of claim 6, wherein the fluid is a pressurized gas.

10. The method of claim 9, wherein the pressurized gas is air, nitrogen, or combination thereof.

11. The method of claim 10, wherein the pressurized gas has a first pressure during extruding the first layer and a second pressure during depositing the mesh layer and extruding the second layer, the second pressure being greater than the first pressure.

12. The method of claim 2, wherein the first layer of material defines the first and second lumens.

13. The method of claim 2, wherein the first lumen is defined by a first tube and the second lumen is defined by a second tube, the first layer of material being extruded over the first and second tubes, the first tube and the second tube each being composed of a different material than the first layer of material of the elongate body.

14. The method of claim 13, wherein each of the first tube and the second tube is composed of a material having a higher durometer than the first layer of material of the elongate body.

15. The method of claim 14, wherein the material of each of the first tube and the second tube is at least one of polyimide, nylons, fluorinated ethylene propylene (FEP), and polyether ether ketone (PEEK).

16. The method of claim 1, wherein:
the elongate body is wound about a first spool after extruding a first layer of material to form an elongate body;
the elongate body is transferred from the first spool to a second spool during depositing a mesh layer over the first layer of material; and
the elongate body is transferred from the second spool to a third spool during extruding a second layer of material over the mesh layer.

17. A method of producing a multi-lumen medical device, the method comprising:
extruding a layer of a first material over a first lumen tube and at least one second lumen tube to form an elongate body having a length of at least 100 feet, a first lumen, and at least one second lumen;
depositing a mesh layer over the layer of first material;
extruding a layer of a second material over the mesh layer, each of the first lumen tube and the at least one second lumen tube at least one of:
being composed of a third material that has a higher durometer than the first material; and
containing a fluid therein.

18. The method of claim 17, wherein the first lumen contains a removable solid core during extruding a layer of first material, depositing a mesh layer, and extruding a layer of second material, the solid core being removed after extruding a layer of second material.

19. The method of claim 18, wherein each of the first lumen tube and the at least one second lumen tube is composed of a third material that has a higher durometer than the first material, the third material being at least one of polyimide, nylons, fluorinated ethylene propylene (FEP), polyether ether ketone (PEEK), and ethylene tetrafluoroethylene (ETFE).

20. The method of claim 18, wherein each of the first lumen tube and the at least one second lumen tube contains a pressurized gas having a first pressure during extruding a layer of a first material and having a second pressure during depositing a mesh layer over the layer of first material and extruding a layer of second material, the first pressure being less than the second pressure.

21. The method of claim 17, further comprising cutting the elongate body into a plurality of shortened elongate bodies, each shortened elongate body having a second length that is less than approximately six feet.

22. The method of claim 21, wherein extruding a second layer of material includes extruding a second layer of material over the mesh layer in one or more sections such that the multi-lumen elongate body includes one or more sections of exposed mesh layer, the elongate body being cut in the sections of exposed mesh layer.

* * * * *